United States Patent
Fellus

(10) Patent No.: US 10,818,198 B2
(45) Date of Patent: Oct. 27, 2020

(54) ORAL DEVICE

(76) Inventor: Patrick Andre Fellus, Paris (FR)

( * ) Notice: Subject to any disclaimer, the term of this patent is extended or adjusted under 35 U.S.C. 154(b) by 619 days.

(21) Appl. No.: 14/000,652

(22) PCT Filed: Dec. 30, 2011

(86) PCT No.: PCT/FR2011/000685
§ 371 (c)(1),
(2), (4) Date: Oct. 4, 2013

(87) PCT Pub. No.: WO2012/120203
PCT Pub. Date: Sep. 13, 2012

(65) Prior Publication Data
US 2014/0024001 A1    Jan. 23, 2014

(30) Foreign Application Priority Data
Mar. 8, 2011  (FR) ...................... 11 00686

(51) Int. Cl.
*G09B 23/28*  (2006.01)
*A61F 5/058* (2006.01)
*A61F 5/56*  (2006.01)

(52) U.S. Cl.
CPC ........ G09B 23/283 (2013.01); A61F 5/05891 (2013.01); A61F 5/566 (2013.01)

(58) Field of Classification Search
USPC ....................................................... 434/262
See application file for complete search history.

(56) References Cited

U.S. PATENT DOCUMENTS

| | | | | |
|---|---|---|---|---|
| 6,129,084 A | * | 10/2000 | Bergersen | A61F 5/566 128/848 |
| 6,203,471 B1 | * | 3/2001 | Akihiro | A63B 23/032 128/859 |
| 6,514,176 B1 | * | 2/2003 | Norton | A63B 23/032 128/848 |
| 2008/0149110 A1 | | 6/2008 | Baldwin | |

FOREIGN PATENT DOCUMENTS

| | | |
|---|---|---|
| DE | 83 23 817 U1 | 3/1984 |
| DE | 20 2009 003914 U1 | 6/2009 |
| EP | 2 189 131 A1 | 5/2010 |

OTHER PUBLICATIONS

International Search Report, dated Apr. 24, 2012, from corresponding PCT application.

* cited by examiner

*Primary Examiner* — James B Hull
(74) *Attorney, Agent, or Firm* — Troutman Pepper Hamilton Sanders LLP

(57) ABSTRACT

An oral device (2) is designed to be worn in the mouth by a person and to stress the trigeminal nerve during swallowing. A method of learning the performance of an action, which includes the wearing of an oral device (2) by a person in order to stress the trigeminal nerve during swallowing.

17 Claims, 2 Drawing Sheets

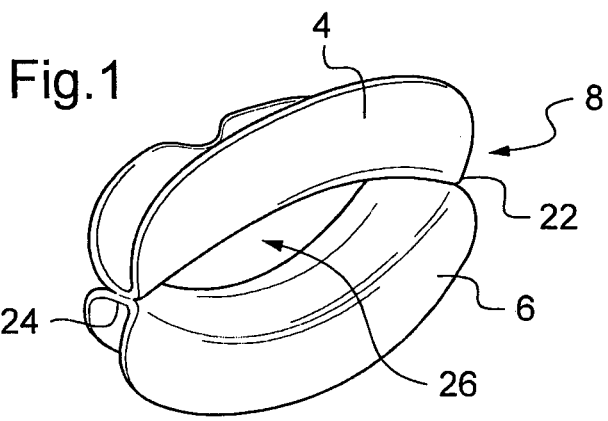
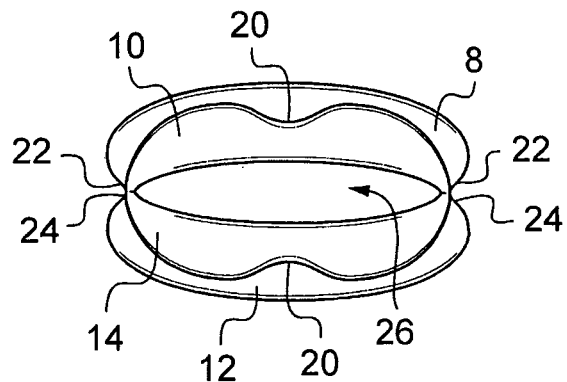
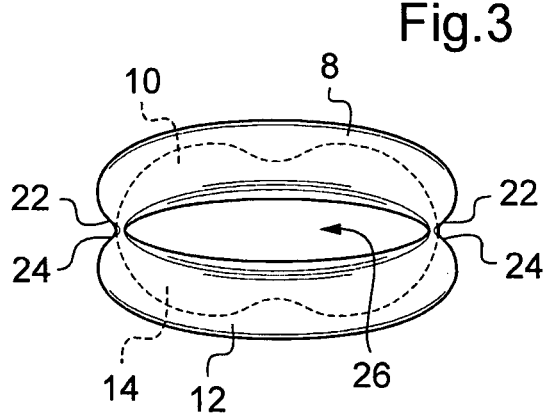
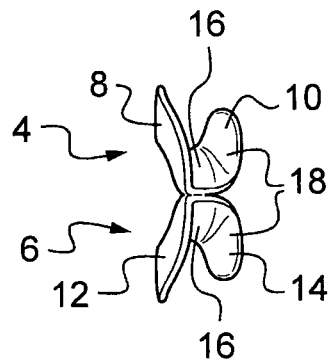
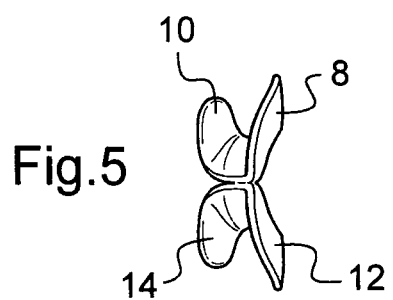

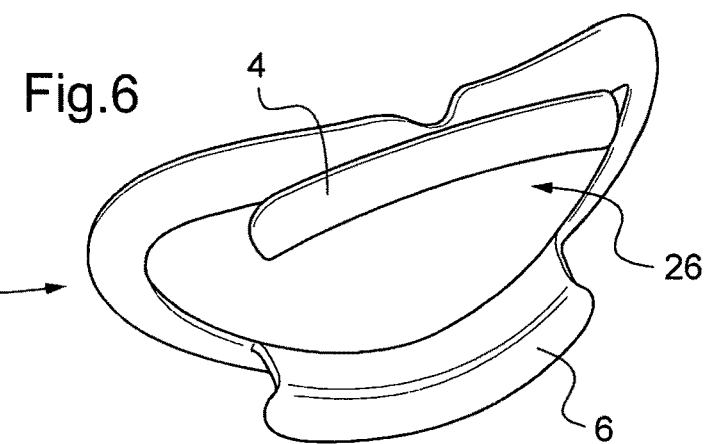
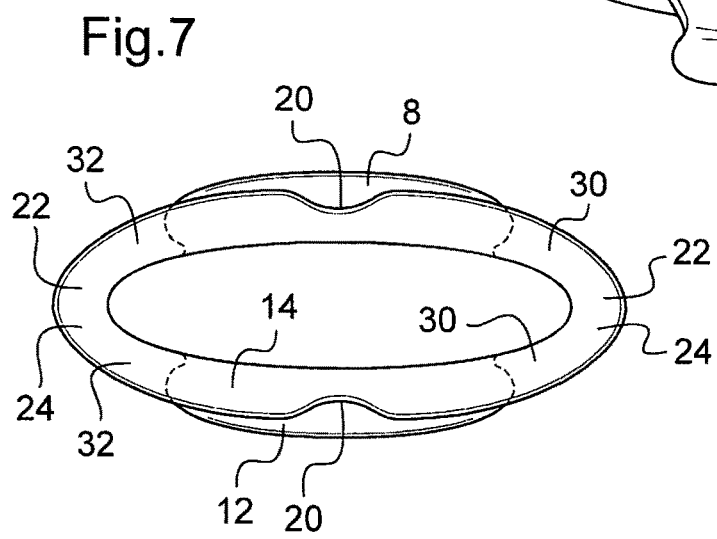
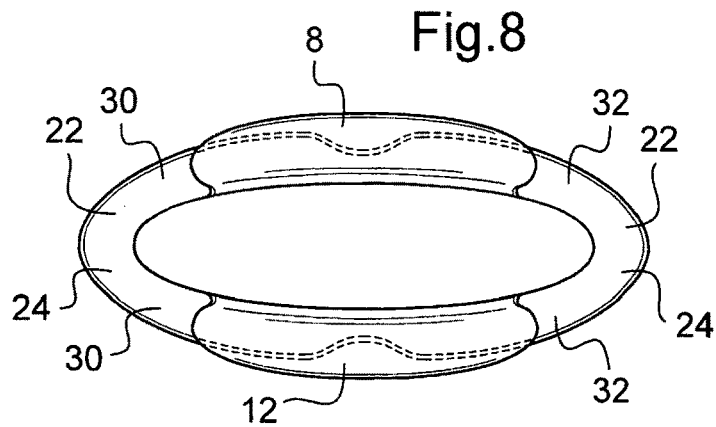
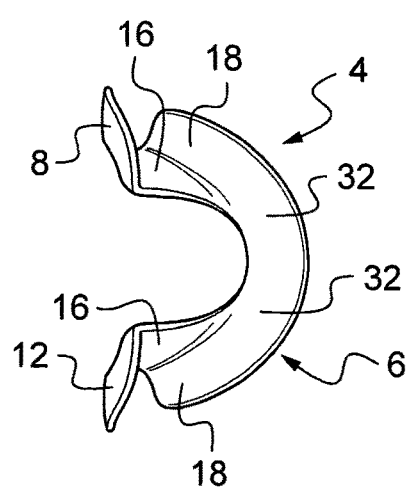
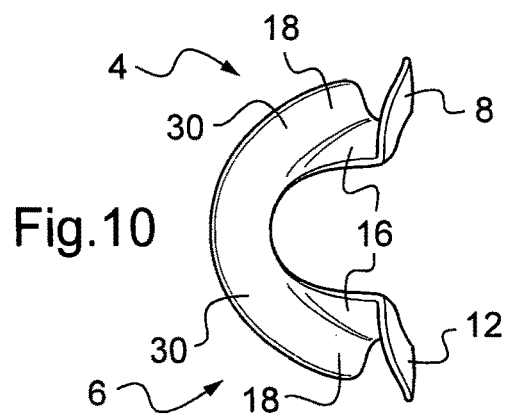

ORAL DEVICE

BACKGROUND OF THE INVENTION

Field of the Invention

The invention relates to the field of facial growth in children.

Description of the Related Art

Facial growth is a field which has been the subject of much research and is perpetually evolving. In the course of this evolution received wisdom is progressively modified and/or overturned.

One well-established dogma is the idea that it is better to wait for maxillo-mandibular growth to be complete, or for all the permanent teeth to have grown, before engaging in any treatment of maxillo-mandibular morphological abnormalities because the size of the mandible is predetermined and it is not possible to influence it.

Clinical research work carried out by the Applicant over the last 25 years have overturned this dogma, and has shown that early orthodontic intervention is a wholly beneficial practice with a view to prevention.

This work does not apply to the treatment of all children having primary teeth, but to the early correction of some skeletal morphological disorders before the conventional age for orthodontic treatment.

Recently the Applicant has identified a set of maxillo-mandibular conditions associated with deficient acquisition of swallowing of the dentitional type (also known as adult swallowing). In practice this means that some children persist with suction-swallowing (also known as infantile swallowing or primary swallowing) for too long.

At the present time this work is at the leading edge in this field and there is no method or device appropriate for its implementation.

BRIEF SUMMARY OF THE INVENTION

This invention will improve the situation.

For this purpose the Applicant provides an oral device designed to be worn by a person in the mouth to stress the trigeminal nerve during swallowing. Advantageously this device may comprise an upper portion having a substantially gutter shape located between a top lip and a dental arch, a lower portion having a substantially gutter shape designed to be located between the lower lip and a dental arch, and an opening between the upper portion and the lower portion. The upper portion and the lower portion are connected together at their respective extremities in such a way that when the device is positioned in the mouth the labial musculature is substantially at rest, and at least part of the opening remains unobstructed.

The Applicant also provides a process for learning a praxis comprising the wearing by a person of an oral device designed to stress the trigeminal nerve during swallowing. Advantageously this process may comprise the fitting of a device at least partly between the person's lips and dental arch, and maintaining the labial musculature substantially at rest while also maintaining an opening between the lips while the device is being worn.

This device and this process have numerous advantages which will be explained below.

BRIEF DESCRIPTION OF THE DRAWINGS

Other features and advantages of the invention will be more apparent from a reading of the following description of examples provided for illustrative and non-restrictive purposes based on the drawings in which:

FIG. 1 shows a perspective view of three-quarters of a device according to the invention, FIG. 2 shows a rear view of the device in FIG. 1, FIG. 3 shows a front view of the device in FIG. 1, FIG. 4 shows a left-hand side view of the device in FIG. 1, FIG. 5 shows a right-hand side view of the device in FIG. 1, FIG. 6 shows a perspective view of three-quarters of another embodiment of the device according to the invention, FIG. 7 shows a rear view of the device in FIG. 6, FIG. 8 shows a front view of the device in FIG. 6, FIG. 9 shows a left-hand side view of the device in FIG. 6, and FIG. 10 shows a right-hand side view of the device in FIG. 6.

The drawings and description below essentially include elements of a particular nature. They can therefore not only be used for a better understanding of this invention, but also to contribute to its definition, as appropriate.

DETAILED DESCRIPTION OF THE PREFERRED EMBODIMENTS

The upper skeletal portion of a child's face grows in a manner which is conditioned by its functional environment. In the case of the orbital cavity, it is the eye which plays the shaping role. In the case of the cranium, it is the brain. As far as the oral cavity is concerned it is the tongue which plays the shaping role, as soon as swallowing of the dentitional type has been acquired.

In fact swallowing of the dentitional type implies that the arch of the tongue rests against the palatal arch in both swallowing movements and normal posture, stimulating transverse growth of the maxilla.

Conventionally children acquire swallowing of the dentitional type between the age of three years and five years, ages at which the milk teeth have formed and chewing habits come to be acquired.

In the case of children who do not acquire swallowing of the dentitional type suction-swallowing persists. But the muscular forces used in suction-swallowing give rise to disturbances in facial growth.

In fact in suction-swallowing the dental arches are not in contact during swallowing movements and the tongue is positioned between the maxilla and the mandible in order to make contact with the labial or jugal mucosa.

Because of this the arch of the tongue ceases to stimulate growth of the palatal arch, which is on the contrary obstructed by depression of the buccinators muscles deriving from the suction movements.

Furthermore contraction of the lower labial and chin musculature holds the mandible in a retracted position, characteristic of functional retromandibulia, which will evolve if it is not corrected into mandibular retrognathy during adolescence. Similarly the fact that the tongue habitually maintains a low position causes the mandible to advance and can therefore transform the initial functional mandibular prognathism into prognathia.

The absence of contact between the tongue and the palatal arch, combined with an inverse incisive function, associates hyperplasia of the middle third with mandibular malformation.

Other unfavourable developmental conditions of the mandible in children can be linked to a deficiency in the acquisition of swallowing of the dentitional type.

In addition to the accompanying physiological problems, these malformations often have major consequences from the psychological point of view because of the aesthetic problems associated with them, which often delay a child's social integration.

Conversely, acquisition of swallowing of the dentitional type encourages the learning of nasal respiration, and an earlier stop to thumb sucking.

All these components contribute to correct growth.

The Applicant's work has demonstrated that transition from suction-swallowing to swallowing of the dentitional type is governed by the establishment of new motor images. In fact habitual movements made without conscious control are carried out on the basis of a sequence of motor images whose elements are as close to each other as the images in a filmed sequence. These new motor images can be acquired by learning, and enrich the body schema in the oral area.

In the present context this schema is based on disconnection of the lips/tongue synkinesis and elevation of the arch of the tongue. Specifically it is a question of learning to swallow without making use of cheek and lip muscles. Disconnection of lip/tongue synkinesis and raising of the arch of the tongue is mainly reflected in a transition from stressing of the facial nerve (VII) in the context of suction-swallowing to stressing of the trigeminal nerve (V) in the context of swallowing of the dentitional type.

It is therefore a matter of teaching the child to abandon suction-swallowing and acquire a new swallowing praxis of the dentitional type. Automation of this type of swallowing, repeated once a minute, will alter the balance of muscular forces and through the 17 muscles constituting it the tongue will thus play the role of a functional shaper.

The Applicant's work has discovered that without this new muscular equilibrium conventional mechanical treatments take longer and the results are not always stable.

At the present time there is no effective method or device which can teach transition from suction-swallowing to swallowing of the dentitional type.

In response to these problems the Applicant has designed the device illustrated in FIG. 1.

As may be seen in this figure, oral device 2 comprises an upper portion 4 and a lower portion 6.

As may be seen in FIGS. 4 and 5, upper portion 4 and lower portion 6 are each substantially gutter shaped. Thus upper portion 4 has a cross-section with a limb 8 and a limb 10 substantially perpendicular to limb 8. Lower portion 6 has a cross-section with a limb 12 and a limb 14 substantially perpendicular to limb 12.

Limb 10 has a curved shape to receive the upper lip, and lodges between the inside surface of the upper lip and the upper dental arch. Limb 14 has a curved shape to receive the lower lip, and lodges between the inside surface of the lower lip and the lower dental arch. The outer surface of the upper lip and the outer surface of the lower lip are in contact with limb 8 and limb 12 respectively.

Limb 10 and limb 14, of curved shape, have two parts:
  a first part 16 which is substantially planar, on which the lower surface of the upper lip and the upper surface of the lower lip respectively bear,
  a second substantially arched part 18 lodged between the inner surfaces of the lips and the dental arch.

First part 16 is substantially planar. First part 16 forms an angle of approximately 90° with limb 8 (and limb 12 respectively). The extremity of first part 16 is curved, so that second part 18 forms an angle with first part 16. The arched shape of second part 18 is arranged so as to match the shape of the dental arch.

As may be seen in FIG. 2, limbs 10 and 14 have a re-entrant or cut-out 20 substantially in the middle of second part 18. Re-entrant 20 is substantially rounded, so that it substantially corresponds to the frenulum of each lip, and facilitates fitting of device 2 in the mouth.

Thus device 2 is secured in the mouth and is held without muscular effort by the lips, offering comfort in use.

As will be more clearly apparent from FIGS. 1, 2 and 3, upper portion 4 and lower portion 6 are connected together at the respective extremities 22 and 24 of portions 18 of limbs 10 and 14 in such a way that between them they define an opening 26 of substantially oval shape. This opening 26 is dimensioned so that it is always at least partly unobstructed when a person wears device 2. In order to achieve this it is designed so that it is thicker than the anterior part of the tongue.

In the embodiment described here upper portion 4 and lower portion 6 are adhesively bonded at extremities 22 and 24. As a variant these extremities comprise cooperating locking members which will allow upper portion 4 to be detached from upper portion 6 when oral device 2 is not worn, and they can be reconnected simply, for example by clipping or any other appropriate means for wearing. In another variant these extremities are welded.

In the embodiment described here device 2 has a total width of 5 cm and opening 26 has a width of approximately 3.5 cm. Limbs 8 and 12 are approximately 1 cm tall and limbs 10 and 14 are approximately 7.5 mm long, curved part 18 of these two limbs rising approximately 4 mm. Opening 26 has a maximum height of approximately 1.5 cm.

In general the width of device 2 is designed to correspond substantially to the space between the commissures of a person's lips. In particular this width may be made slightly greater to facilitate holding without stressing the muscles. Opening 26 is designed to be larger than the apex of the tongue. In order to accommodate all mouths the device may be provided in several sizes, for example three sizes. As a variant, these different sizes may be obtained using cooperating locking members of different sizes, or telescopic members.

Upper portion 4 and lower portion 6 each have a plane of symmetry substantially perpendicular to the plane of FIGS. 2 and 3 at the location of re-entrant 20. This plane of symmetry reflects the symmetry of the human mouth. Furthermore device 2 may in some cases have an additional plane of symmetry, also perpendicular to the plane of FIGS. 2 and 3, but this time at opening 26, so that upper portion 4 and lower portion 6 are symmetrical with each other in relation to that plane.

As a variant the upper portion and the lower portion may each have a larger gutter width distally from the opening than proximally to the opening to permit better holding and to ease fitting. In other words the profiles of the upper and lower portions may be flared.

FIGS. 6 to 10 show a second embodiment of the oral device. In this variant oral device 2 is of one piece and is for example made by moulding or by any other appropriate means. Thus limbs 10 and 14 each comprise a third part 30 and a fourth part 32.

As may be seen in FIGS. 7 and 8, third parts 30 and fourth parts 32 are substantially symmetrical with each other in relation to a plane substantially perpendicular to the plane of FIGS. 7 and 8 at re-entrant 20 and are extensions of second parts 18 on either side of the latter.

Third part 30 of limb 10 is connected to third part 30 of limb 14, and fourth part 32 of limb 10 is connected to fourth part 32 of limb 14.

In this variant device 2 has a total width of 8.5 cm. Opening 26 is of a generally oblong shape and has a maximum height of approximately 2 cm and a maximum width of approximately 7.5 cm. Limbs 8 and 12 have a height of approximately 1 cm and a width of approximately 3 cm. Parts 16 of limbs 10 and 14 extend over a depth of approximately 7.5 mm and curved parts 18 rise approximately 4 mm.

These dimensions may vary according to the selected size of device 2, that is in relation to the dimensions of a child's mouth. Thus the total width of the device may be between 3 cm and 10 cm, opening 26 may have a maximum width between 2 cm and 9 cm, and a maximum height of between 3 mm and 4.5 cm. Limbs 8 and 12 may have a height of between 5 mm and 2 cm, and a width of between 2 cm and 5 cm, that is a value close to the distance between the commissures. Part 16 of limbs 10 and 14 may extend over a depth of between 3 mm and 3 cm, and curved part 18 may rise between approximately 2 mm and 1 cm. These dimensions may be applied to the embodiment in FIGS. 1 to 5.

Advantageously the linking portion of parts 30 and 32 substantially matches the internal contour of the lips, and the connection takes place at the modioli of the commissure of the cheeks, thus opposing contraction of the muscles at this point.

It follows from the two embodiments described that:
upper portion 4 and lower portion 6 have a substantially gutter shape,
the remainder of the device is arranged in a manner posterior to a plane defined by one of the edges of these gutters, beyond the portion connecting the edges of these gutters.

By a substantially gutter shape is meant the fact that the assembly of limbs 8 and 10 and the assembly of limbs 12 and 14 hold the lips in the manner of a gutter. Thus the lips are substantially at rest and their contraction is opposed.

However it would be possible to lighten some of these limbs either partly or extensively while retaining this function, for example by removing material or by making the limbs in the form of a grille. Such embodiments fall within the scope of the invention.

The Applicant's work has demonstrated that wearing of device 2 by a person and in particular a child is only slightly inconveniencing, but conversely makes it possible to acquire swallowing of the dentitional type spontaneously.

In fact device 2 holds the upper and lower lips at a distance from each other, preventing a sealing joint being made between the two lips through opening 26, which prevents negative pressure from being set up within the mouth cavity by suction. As a reaction the person can only raise the posterior portion of their tongue towards the palatal arch, and thus acquire this new praxis.

Furthermore device 2 is held in the mouth without contraction of the orbicular musculature. Thus as these muscles are substantially at rest the facial nerve is only stimulated partly or not at all during swallowing. This makes it possible to learn a praxis in which the trigeminal nerve is the main nerve stimulated.

Use of device 2 is therefore particularly advantageous because this learning is accomplished without conscious work on the part of the person, using pre-existing neurological wiring which has never been stimulated. This means that no special exercise or specific action is needed, apart from the wearing of device 2.

The process of learning the praxis described here comprises the wearing of device 2 by a person for a time of between 5 minutes and 15 minutes. This process should be performed daily over a minimum period of one week and up to a maximum period of 3 months. The process may be stopped once the praxis has been acquired, that is to say as soon as the action has become automatic.

Use of device 2 may be seen as a process of learning a swallowing praxis comprising stressing of the trigeminal nerve, and in general as a process of enlarging the palatal arch.

Furthermore the application of this process does not require action by any medical personnel, nor any particular treatment, because all that is necessary is to place the device in the mouth.

At the present time this work is at the leading edge in this domain and there is no suitable method or device appropriate for such an application.

The Applicant has developed a device for learning adult swallowing. The device is an aid to learning the praxis of adult swallowing. The device stresses the trigeminal nerve. The device alters the balance between the muscles. From another point of view the invention relates to a device which conditions habitual movements not under conscious control through new motor images. The device is an anti-suction or anti-primary swallowing device. Through this effect the device is also a tool for correcting skeletal malformations.

Device 2 may be provided for example in three models of different sizes, known as the small size model, the middle size model and the large size model. In general device 2 may have the following dimensions:
a total width, that is an external distance between extremities 22 and 24, of between 3 cm and 5.5 cm,
between 3.2 cm and 4 cm for the small size model, for example 3.6 cm,
between 3.8 cm and 4.6 cm for the middle size model, for example 4.2 cm, and
between 4.5 cm and 5.5 cm for the large size model, for example 5 cm;
a width of opening 26, that is to say an interior distance between extremities 22 and 24, of between 2 cm and 5 cm,
between 2.2 cm and 3.2 cm for the small size model, for example 2.7 cm,
between 2.8 cm and 3.8 cm for the middle size model, for example 3.3 cm, and
between 3.3 cm and 4.3 cm for the large size model, for example 3.8 cm;
a width of opening 26, that is to say substantially half way between respective extremities 22 and 24, of between 3 cm and 25 cm,
between 3 cm and 8 cm for the small size model, for example 7 cm,
between 5 cm and 12 cm for the middle size model, for example 10 cm, and
between 10 cm and 20 cm for the large size model, for example 15 cm;
a height of limbs 8 and 12 of between 5 mm and 20 mm,
between 8 mm and 16 mm for the small size model, for example 12 mm,
between 9 mm and 17 mm for the middle size model, for example 13 mm, and
between 10 mm and 18 mm for the large size model, for example 14 mm;
a width of limbs 8 and 12 equivalent to the total width of the device, or between 2 cm and 5 cm, between 2 cm and 2.5 cm for the small size model, for example 2.2 cm, between 3 cm and 3.5 cm for the middle size model, for example 3.2 cm, and between 4 cm and 4.5 cm for the large size model, for example 4.2 cm;

a depth between parts 16 of limbs 10 and 14, that is to say the width of the base of the gutters, of between 3 mm and 30 mm, between 5 mm and 15 mm for the small size model, for example 11 mm, between 8 mm and 14 mm for the middle size model, for example 12 mm, and between 12 mm and 20 mm for the large size model, for example 13 mm; and a height of curved portions 18, away from re-entrant 20, of between 2 mm and 20 mm, between 4 mm and 14 mm for the small size model, for example 9 mm, between 5 mm and 15 mm for the middle size model, for example 10 mm, and between 8 mm and 18 mm for the large size model, for example 13 mm.

The thickness of each of the parts of device 2 may comprise walls of thickness between 0.2 mm and 2 mm, for example 1.5 mm.

The invention claimed is:

1. An oral device configured to be worn by a person in the mouth to stress the trigeminal nerve when swallowing, the oral device comprising:
    an upper portion having a substantially gutter shape and configured to be disposed between an upper lip and an upper dental arch, the upper portion comprising an outer limb and an inner limb, the inner limb of the upper portion having a cut-out shaped to accommodate a frenulum of the upper lip;
    a lower portion having a substantially gutter shape and configured to be disposed between a lower lip and a lower dental arch, the lower portion comprising an outer limb and an inner limb, the inner limb of the lower portion having a cut-out shaped to accommodate a frenulum of the lower lip; and
    an opening between the upper portion and the lower portion, the opening having a maximum height of 1.5 cm,
    wherein the upper portion and the lower portion are connected together at respective extremities so that when the device is positioned in the mouth a labial musculature is substantially at rest and at least part of the opening remains unobstructed,
    wherein the upper and lower portions prevent the lips from closing and elevates an arch of the tongue when the user swallows so that the trigeminal nerve (V) is mainly stimulated; and
    wherein the connection between the upper portion and the lower portion is at least partially discontinuous.

2. The device according to claim 1, wherein at least one of the two limbs of the upper portion or the two limbs of the lower portion form a housing for the labial musculature.

3. The device according to claim 1, wherein the opening has a substantially oblong shape.

4. The device according to claim 1, wherein the maximum height is between 3 mm and 1.5 cm.

5. The device according to claim 1, wherein the opening has a maximum width of between at least one of 2 cm and 9 cm and between 3 mm and 10 cm.

6. The device according to claim 1, wherein the upper portion and the lower portion each have a greater thickness distally from the opening than proximally to the opening.

7. The device according to claim 2, wherein the opening has a substantially oblong shape.

8. The device according to claim 2, wherein the opening has a maximum height of between 3 mm and 1.5 cm.

9. The device according to claim 2, wherein the opening has a maximum width of between 2 cm and 9 cm.

10. The device according to claim 3, wherein the opening has a maximum width of between 2 cm and 9 cm.

11. The device according to claim 1, wherein the connection between the upper and lower portions comprises:
    a discontinuous portion between both the upper inner limb and the lower inner limb and the upper outer limb and the lower outer limb.

12. The device according to claim 1, wherein the connection between the upper and lower portions comprises:
    a continuous section connecting the upper inner limb and the lower inner limb; and
    a discontinuous section between the upper outer limb and the lower outer limb.

13. A method to stress a trigeminal nerve in a user during swallowing, comprising the steps of:
    forming an upper portion of an oral device having a substantially gutter shape to be disposed between an upper lip and an upper dental arch, comprising the steps of:
        forming an upper portion outer limb; and
        forming an upper portion inner limb comprising a cut-out shaped to accommodate a frenulum of the upper lip;
    forming a lower portion of the oral device having a substantially gutter shape and configured to be disposed between a lower lip and a lower dental arch, comprising the steps of:
        forming a lower portion outer limb; and
        forming a lower portion inner limb, the inner limb comprising a cut-out shaped to accommodate a frenulum of the lower lip; and
    designing an opening between the upper portion and the lower portion; and
    preventing, using the oral device, lips of the user from closing and elevating an arch of the tongue when the user swallows, while keeping lips substantially at rest so that the trigeminal nerve (V) is mainly stimulated.

14. The method of claim 13, wherein the designing step comprises the step of forming the opening larger than the apex of the tongue of the user.

15. The method of claim 13, further comprising the steps of:
    connecting the upper portion and the lower portion together at respective extremities; and
    positioning the device in a mouth of the user so a labial musculature is substantially at rest and at least part of the opening remains unobstructed.

16. The method of claim 13, wherein the preventing step comprises the step of preventing negative pressure within the mouth when the user engages in a sucking activity during swallowing.

17. The method of claim 13, wherein the forming of the upper portion and the lower portion further comprises the step of configuring the upper and the lower portions of the oral device to be held in the mouth without contraction of the orbicular musculature.

\* \* \* \* \*